US007065453B1

(12) United States Patent
Diller et al.

(10) Patent No.: US 7,065,453 B1
(45) Date of Patent: Jun. 20, 2006

(54) MOLECULAR DOCKING TECHNIQUE FOR SCREENING OF COMBINATORIAL LIBRARIES

(75) Inventors: David J. Diller, East Windsor, NJ (US); Kenneth M. Merz, Jr., State College, PA (US)

(73) Assignee: Accelrys Software, Inc., San Diego, CA (US)

( * ) Notice: Subject to any disclaimer, the term of this patent is extended or adjusted under 35 U.S.C. 154(b) by 0 days.

(21) Appl. No.: 09/595,096

(22) Filed: Jun. 15, 2000

(51) Int. Cl.
  G06G 7/48 (2006.01)
  G06N 7/06 (2006.01)
(52) U.S. Cl. ............................................. 702/27; 703/2
(58) Field of Classification Search ................. 435/7.1; 702/19, 27; 395/500.23; 703/2
  See application file for complete search history.

(56) References Cited

U.S. PATENT DOCUMENTS

| 5,463,564 | A | 10/1995 | Agrafiotis et al. ........... 364/496 |
| 5,495,423 | A | 2/1996 | DeLisi et al. ............... 364/496 |
| 5,854,992 | A | 12/1998 | Shakhnovich et al. ........ 702/27 |
| 5,889,528 | A * | 3/1999 | Zhao .......................... 345/648 |
| 2002/0025535 | A1 | 2/2002 | Diller et al. ................. 435/7.1 |
| 2003/0228624 | A1 | 12/2003 | Diller et al. ................. 435/7.1 |

FOREIGN PATENT DOCUMENTS

| WO | WO 98/04913 | 2/1998 |
| WO | WO 01/97098 A2 | 12/2001 |

OTHER PUBLICATIONS

McMartin et al. QXP: Powerful, rapid computer algorithms for structure-based drug design. J. Computer-Aided Molecualr Design (1997) vol. 11, No. 4, pp. 333-344.*
Wang et al. Flexible ligand docking: A multistep strategy approach. Proteins (1999) vol. 36, No. 1, pp. 1-19.*
M. Rarey, S. Wefing & T. Lengauer, "Placement of medium-sized molecular fragments into active sites of proteins", Journal of Computer-Aided Molecular Design. 10 (1996) 41 54, 1996 ESCOM Science Publishers B.V., pp. 41-54.
D.K. Gehlhaar, G.M. Verkhivker, P.A. Rejto, C.J. Sherman, D.B. Fogel, L.J. Fogel & S.T. Freer, "Molecular recognition of the inhibitor AG-1343 by HIV-1 protease: conformationally flexible docking by evolutionary programming", Current Biology Ltd ISSN 1074-5521, Chemistry & Biology, (1995), vol. 2 No. 5, pp. 317-324.
P.J. Goodford, "A Computational Procedure for Determining Energetically Favorable Binding Sites on Biologically Important Macromolecules", Journal of Medicinal Chemistry, 1985, vol. 28, No. 7, (1985) American Chemical Society, pp. 849-857.

C.A. Baxter, C.W. Murray, D.E. Clark, D.R. Westhead & M.D. Eldridge, "Flexible Docking Using Tabu Search and an Empirical Estimate of Binding Affinity", PROTEINS: Structure, Function, and Genetics 33:367-382 (1998), 1998 Wiley-Liss, Inc., pp. 367-382.
G. Jones, P. Willett, R.C. Glen, A.R. Leach & R. Taylor, "Development and Validation of a Genetic Algorithm for Flexible Docking", JMB, J. Mol. Biol. (1997), 267, 727-748, 1997 Academic Press Limited, pp. 726-748.
M. Rarey, B. Kramer & T. Lengauer, "The Particle Concept: Placing Discrete Water Molecules During Protein-Ligand Docking Predictions", PROTEINS: Structure, Function, and Genetics 34:17-28 (1999), 1999 Wiley-Liss, Inc., pp. 17-28.
B. Kramer, M. Rarey & T. Lengauer, "Evaluation of the FlexX Incremental Construction Algorithm for Protein-Ligand Docking", PROTEINS: Structure, Function, and Genetics 37:228-241 (1999), 1999 Wiley-Liss, Inc., pp. 228-241.
Welch et al., Hammerhead: Fast, Fully Automated Docking Of Flexible Ligands To Protein Binding Sites, Chemistry & Biology, Jun. 1996, vol. 3, pp. 449-462.
Rarey, et al., A Fast Flexible Docking Method Using an Incremental Construction Algorithm, J. Mol. Biol., 1996, 261, pp. 470-489.
Jones et al., Development and Validation of a Genetic Algorithm for Flexible Docking, J. Mol., Biol., 1997, 267, pp. 727-748.
Sun et al., CombiDOCK: Structure-based Combinatorial Docking and Library Design, Journal of Computer-Aided Molecular Design, 1998, vol. 12, pp. 597-604.
Diller et al., High Throughput Docking for Library Design and Library Prioritization, PROTEINS: Structure, Function, and Genetics, 2001, 43, pp. 113-124.

(Continued)

Primary Examiner—Marjorie A. Moran
(74) Attorney, Agent, or Firm—Knobbe Martens Olson & Bear LLP

(57) ABSTRACT

A high-throughput molecular docking facility is presented for screening combinatorial libraries to identify binding ligands and ultimately pharmaceutical compounds. The facility employs a pre-docking conformational search to generate multiple solution conformations of a ligand. The molecular docking facility includes: generating a binding site image of the protein, the binding site image having multiple hot spots; matching hot spots of the binding site image to atoms in at least one solution conformation of the multiple solution conformations of the ligand to obtain at least one ligand position relative to the protein in a ligand-protein complex formation; and optimizing the at least one ligand position while allowing translation, orientation and rotatable bonds of the ligand to vary, and while holding the protein fixed.

2 Claims, 8 Drawing Sheets

OTHER PUBLICATIONS

Ho et al., *De novo* design of ligands, Proceedings of the Twenty-Seventh Annual Hawaii International Conference on Systems Sciences, 1994.

Kirkpatrick, et al., Optimization by Simulated Annealing, SCIENCE, vol. 220, No. 4598, May 13, 1983, pp. 671-680.

Makino et al., DREAM++: Flexible Docking Program for Virtual Combinatorial Libraries; Journal of Computer-Aided Molecular Design, 13, 513-532, 1999.

Rarey et al., A Recursive Algorithm for Efficient Combinatorial Library Docking, Perspectives in Drug Discovery and Design, 20: 63-81, 2000.

Shah et al., Structural Consensus in Ligand-Protein Docking Identifies Recognition Peptide Motifs That Bind Streptavidin, PROTEINS: Structures, Function, and Genetics, 28: 421-433 (1997).

Aldenderfer et al., Cluster Analysis, Sage University Paper, pp. 33-40, 1984.

Drenth, Principles in Protein X-Ray Crystallography, 1995, Springer-Verlag, p. 16.

News Focus, Tapping DNA for Structures Produces a Trickle, Science, Nov. 1, 2002, vol. 298, pp. 948-950.

* cited by examiner

MOLECULAR DOCKING TECHNIQUE FOR SCREENING OF COMBINATORIAL LIBRARIES

TECHNICAL FIELD

The present invention relates in general to screening combinatorial libraries by identification of binding ligands and ultimately pharmaceutical compounds, and more particularly, to a high throughput molecular docking technique for screening of combinatorial libraries.

BACKGROUND OF THE INVENTION

Prediction of small molecule binding modes to macromolecules of known three-dimensional structure is a problem of paramount importance in rational drug design (the "docking"problem) . . . Protein binding sites exhibit highly selective recognition of small organic molecules, in that evolution has equipped them with a complex three-dimensional "lock" into which only specific "keys" will fit. This has been exploited by medicinal chemists in the design of molecules to selectively augment or retard biochemical pathways and so exhibit a clinical effect. X-ray crystallography has revealed the structure of a significant number of these binding sites. It would be advantageous in attempting the computer-aided design of therapeutic molecules to be able to predict and to explain the binding mode of novel chemical entities (the "docking" problem) when the active site geometry is known." (Jones et al. *J. Mol. Bio.* 267, pg. 727 (1997)) With the advent of combinatorial chemistry and the resulting ability to synthesize large collections of compounds for a broad range of targets, it has become apparent that the capability to effectively prioritize screening efforts is crucial to the rapid identification of the appropriate region of chemical space for a given target. Since it has been generally observed that hits obtained against a given target are clustered in a finite region of chemical space, there is reason to believe that given the right computational tools it is possible to prioritize screening efforts such that only libraries containing active compounds are interrogated. Effective prioritization tools would allow scientists to both obtain leads in a cost effective and efficient manner and to test virtual libraries against novel targets prior to active synthesis and bioanalysis, thereby, reducing synthesis costs. With the expected flood of new targets becoming available in the coming decade, it will be critical to focus screening efforts on target appropriate regions of chemical space.

There are many challenges to overcome prior to being able to develop appropriate library prioritization tools. At one extreme are the screens for which there is no structural data for the target. In these cases, QSAR or other data mining tools are typically the method of choice for screening prioritization. At the opposite extreme are the structure-based approaches that rely on the availability of X-ray structures of the target. Unfortunately, in most cases, a crystal structure is not available. With the advent of proteomics and high-throughput protein crystallography, however, it is likely that for a given target, a structure of a related protein will be available. In these cases, a homology model can be built starting from the structure of a related protein, and structure-based tools could be utilized in conjunction with QSAR or other data mining tools.

When structural information for a target protein is available, molecular docking can be a useful tool for prioritizing screening efforts (reference: Charifson, P. S., ed. *Practical Application of Computer-aided Drug Design* 1997, Marcel Dekker: New York. 551; Knegtel, R. M. A. and M. Wagener, "Efficacy and Selectivity in Flexible Database Docking," PROTEINS: Structure, Function and Genetics, 1999, Vol. 37, p. 334–345; and Debnath, A. K., L. Radigan, and S. Jiang, "Structure-based Identification of Small Molecule Antiviral Compounds Targeted to the gp41 Core Structure of the Human Immunodeficiency Virus Type 1," Journal of Medicinal Chemistry, 1999, Vol. 42(17), p. 3202–3209). Operationally, this means that rather than assaying an entire collection of compounds, the compounds are first docked and ranked via some scoring function, and then only a subset of the compounds, usually the highest ranked, are assayed. This approach to prioritizing screening efforts usually increases by a factor of 1–10 the number of active compounds, i.e., when compared to a randomly selected subset of compounds, (see, Charifson, P. S., et al., "Consensus Scoring: A Method for Obtaining Improved Hit Rates From Docking Databases of Three-dimensional Structures Into Proteins," Journal of Medicinal Chemistry, 1999, Vol. 42(25), p. 5100–5109).

The ultimate goal of this invention is to use molecular docking as a way to prioritize combinatorial library screening efforts, i.e., rather than ranking individual compounds, combinatorial libraries of compounds are ranked. Compounds synthesized through combinatorial methods are often quite flexible when compared to typical databases of compounds used for molecular docking studies. Thus, for a docking procedure to be useful, it should be able to handle fairly flexible compounds (as many as 10–20 rotatable bonds), and it should be extremely fast (on the order of one million compounds a week). With these constraints in mind, a new docking technique has been developed and validated, as presented hereinbelow.

DISCLOSURE OF THE INVENTION

To briefly summarize, presented herein in one aspect is a method of docking a ligand to a protein. The method includes: performing a pre-docking conformational search to generate multiple solution conformations of the ligand; generating a binding site image of the protein, the binding site image comprising multiple hot spots; matching hot spots of the binding site image to atoms in at least one solution conformation of the multiple solution conformations of the ligand to obtain at least one ligand position relative to the protein; and optimizing the at least one ligand position while allowing translation, orientation and rotatable bonds of the ligand to vary, and while holding the protein itself fixed.

In another aspect, a system for docking a ligand to a protein is provided. The system includes means for performing a pre-docking conformational search to generate multiple solution conformations of the ligand. In addition, the system includes means for generating a binding site image of the protein, with the binding site image comprising multiple hot spots; and means for matching hot spots of the binding site image to atoms in at least one solution conformation of the multiple solution conformations of the ligand to obtain at least one ligand position relative to the protein. An optimization mechanism is also provided for optimizing the at least one ligand position while allowing translation, orientation and rotatable bonds of the ligand to vary, and while holding the protein fixed.

In a further aspect, the invention comprises at least one program storage device readable by a machine, tangibly embodying at least one program of instructions executable by the machine to perform a method of docking a ligand to a protein. The method includes: performing a pre-docking conformational search to generate multiple solution conformations of the ligand; generating a binding site image of the protein, the binding site image comprising multiple hot spots; matching hot spots of the binding site image to atoms in at least one solution conformation of the multiple solution conformations of the ligand to obtain at least one ligand position relative to the protein; and optimizing the at least one ligand position while allowing translation, orientation and rotatable bonds of the ligand to vary, and while holding the protein fixed.

The docking method presented herein has several advantages. First, it is built from several independent pieces. This allows one to better take advantage of scientific breakthroughs. For example, when a better conformational search procedure (in the present context this means more biologically relevant conformers) becomes available, it can be used to replace the current conformational search procedure by generating new 3-D databases. Second, this approach to ligand flexibility is better suited for the class of compounds synthesized through combinatorial methods. Compounds from combinatorial libraries frequently do not have a clear anchor fragment. Because finding and docking an anchor fragment from the ligand are key steps in the incremental construction algorithms, these algorithms may encounter difficulties with compounds commonly found in combinatorial libraries. (Incremental construction algorithms work roughly as follows: the ligand is divided into rigid fragments; the largest of these fragments is docked into the binding site of the protein; and the ligand is then rebuilt in the binding site by attaching the appropriate fragments and systematically searching around the rotatable bonds. The procedure is described further in: M. Rarey, B. Kramer, T. Lengauer, & G. Klebe, "A fast flexible docking method using an incremental construction algorithm", J. Molecular Biology, 261 (1996), pp. 470–489; and S. Makino & I. Kuntz, "Automated flexible ligand docking method and its application to database search", J. Computational Chemistry, 18 (1997), pp. 1812–1825.) Docking entire conformations overcomes this difficulty. In addition, including an efficient flexible optimization step removes a significant burden from the conformational search procedure. Further improvements in energy minimization algorithms can also be taken advantage of, as they become available.

The approach herein to ligand flexibility could be viewed as a liability because of a reliance on an initial conformational search. As indicated previously, in order to achieve maximum efficiency the conformational search should be performed once for an entire library or collection and the resulting conformations stored for future use. For large collections, this would be a considerable investment in both computer time and disk space. Because a database will typically be used many times, the initial computer time for the conformational search can easily be justified. Moreover, with the availability of parallel computers and faster CPUs, the conformational search can be completed or occasionally redone in a reasonable amount of time. Since disk sizes are now approaching the tera-byte level, storing the conformations for millions of compounds presents no problem.

BRIEF DESCRIPTION OF THE DRAWINGS

The above-described objects, advantages and features of the present invention, as well as others, will be more readily understood from the following detailed description of certain preferred embodiments of the invention, when considered in conjunction with the accompanying drawings in which.

BEST MODE FOR CARRYING OUT THE INVENTION

Figure 1A:
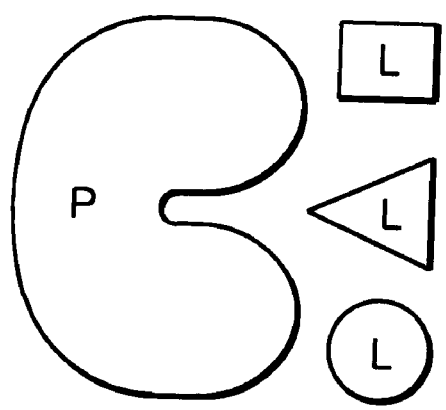
FIGS. 1A–1C conceptually depict protein-ligand complex formation.
Figure 1B:
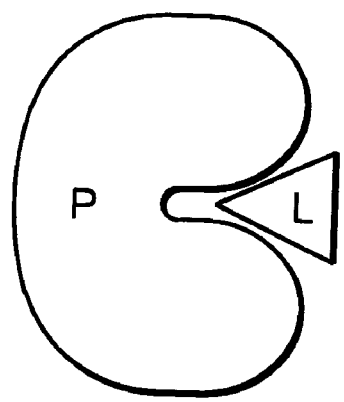
Figure 1C:
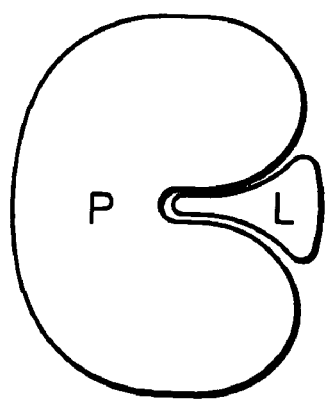

The docking procedure discussed below is based on a conceptual picture of protein-ligand complex formation (see FIGS. 1A–1C). Initially, the ligand (L) adopts many conformations in solution. The protein (P) recognizes one or several of these conformations. Upon recognition, the ligand, protein and solvent follow the local energy landscape to form the final complex.

This simple picture of protein/ligand complex formation is converted into an efficient computational model in accordance with an aspect of the present invention, as follows. The initial solution conformations are generated using a straightforward conformational search procedure. One might view the conformational search part of this technique as part of the entire docking process, but since it involves only the ligand, it can be decoupled from the purely docking steps. This is justified since 3-D databases of conformations for a collection of molecules can readily be generated and stored for use in numerous docking studies (for example, using Catalyst, see A. Smellie, S. D. Kahn, S. L. Teig, "Analysis of Conformational Coverage. 1. Validation and Estimation of Coverage", J. Chem. Inf. Comput. Sci. (1995) v235, pp285–294; and A. Smellie, S. D. Kahn, S. L. Teig, "Analysis of Conformational Coverage. 2. Application of Conformational Models", J. Chem. Inf. Comput. Sci. (1995) v235, pp295–304). The recognition stage is modeled by matching atoms of the ligand to interaction of "hot spots" in the binding site. The final complex formation is modeled using a gradient based optimization technique with a simple energy function. During this final stage, the translation, orientation, and rotatable bonds of the ligand are allowed to vary, while the protein and solvent are held fixed.

Most docking methods can be classified into one of two loosely defined categories: (1) stochastic, such as AutoDock, (Goodford, P. J., "A Computational Procedure for Determining Energetically Favorable Binding Sites on Biologically Important Macromolecules," Journal of Medicinal Chemistry, 1985, Vol. 28(7), p. 849–857; Goodsell, D. S. and A. J. Olson, "Automated Docking of Substrates to Proteins by Simulated Annealing," PROTEINS: Structure, Function and Genetics, 1990, Vol. 8, p. 195–202), GOLD (Jones, G., et al., "Development and Validation of a Generic Algorithm for Flexible Docking," Journal of Molecular Biology, 1997, Vol. 267, p. 727–748), TABU (Westhead, D. R., D. E. Clark, and C. W. Murray, "A Comparison of Heuristic Search Algorithms for Molecular Docking," Journal of Computer-Aided Molecular Design, 1997, Vol. 11, p. 209–228; and Baxter, C. A. et al., "Flexible Docking Using Tabu Search and an Empirical Estimate of Binding Affinity," PROTEINS: Structure, Function, and Genetics, 1998, Vol. 33, p. 367–382), and Stochastic Approximation with Smoothing (SAS) (Diller, D. J. and C. L. M. J. Verlinde, "A Critical Evaluation of Several Global Optimization Algorithms for the Purpose of Molecular Docking," Journal of Computational Chemistry, 1999, Vol. 20(16), p. 1740–1751); or (2) combinatorial, for example, DOCK (Kuntz, I. D., et al., "A Geometric Approach to Macromolecular-ligand Interactions," Journal of Molecular Biology, 1982, Vol. 161, p. 269–288); Kuntz, I. D., "Structure-based Strategies for Drug Design and Discovery," Science, 1992, Vol. 257, p. 1078–1082; Makino, S. and I. D. Kuntz, "Automated Flexible Ligand Docking Method and Its Application for Database Search," Journal of Occupational Chemistry, 1997, Vol. 18(4), p. 1812–1825), FlexX (Rarey, M., et al., "A Fast Flexible Docking Method Using an Incremental Construction Algorithm," Journal of Molecular Biology, 1996, Vol. 261, p. 470–489; Rarey, M., B. Kramer, and T. Lengauer, "The Particle Concept: Placing Discrete Water Molecules During Protein-ligand Docking Predictions," PROTEINS: Structure, Function, and Genetics, 1999, Vol. 34, p. 17–28; Rarey M., B. Kramer, and T. Lengauer, "Docking of Hydrophobic Ligands With Interaction-based Matching Algorithms," Bioinformatics, 1999, Vol. 15(3), p. 243–250), and HammerHead (Welch, W., J. Ruppert, and A. N. Jain, "Hammerhead: Fast Fully Automated Docking of Flexible Ligands to Protein Binding Sites," Chemistry & Biology, 1996, Vol. 3(6), p. 449–462).

The stochastic methods, while often providing more accurate results, are typically too slow to search large databases. The method presented herein falls into the combinatorial group. This approach is analogous to FlexX and HammerHead in that it attempts to match interactions between the ligand and receptor. It differs from these and most other docking techniques significantly in how it handles the flexibility of the ligand. Most current combinatorial docking techniques handle flexibility using an incremental construction approach, whereas the technique described herein uses an initial conformational search followed by a gradient based minimization in the presence of the target protein.

Figure 2:
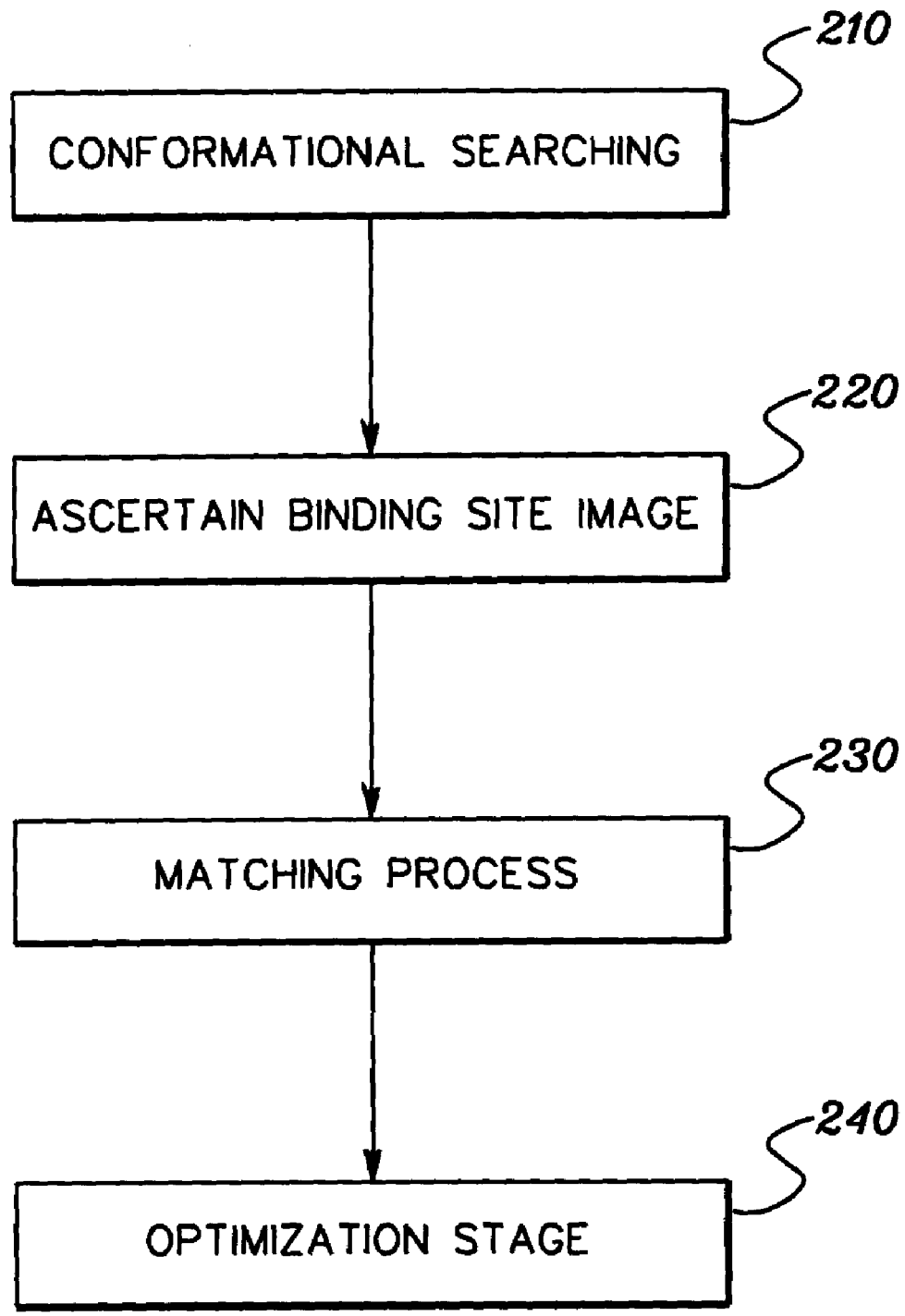
FIG. 2 is a flowchart of one embodiment of a molecular docking approach in accordance with the principles of the present invention.

A generalized technique of one embodiment of the present invention is depicted in FIG. 2. Initially, a conformational search procedure 210 is performed for an entire library or collection, with the resulting conformations stored for future use. A binding site image is then created using the protein structure 220. A matching procedure is performed to form an initial complex by initially positioning a given conformation of a ligand as a rigid body into the binding site 230. Finally, a flexible optimization is performed wherein the matches are pruned and then optimized to attain the final result 240. Each of these steps of a docking approach, in accordance with the present invention, is described in greater detail below with reference to FIGS. 3–6, respectively.

The Conformational Search Procedure

For one aspect of the present invention, a straightforward yet effective conformational search procedure is preferred. A conformational search is performed once for an entire library or a collection, with the resulting conformations stored for future use. If desired, the conformational searching can be periodically repeated.

Figure 3:
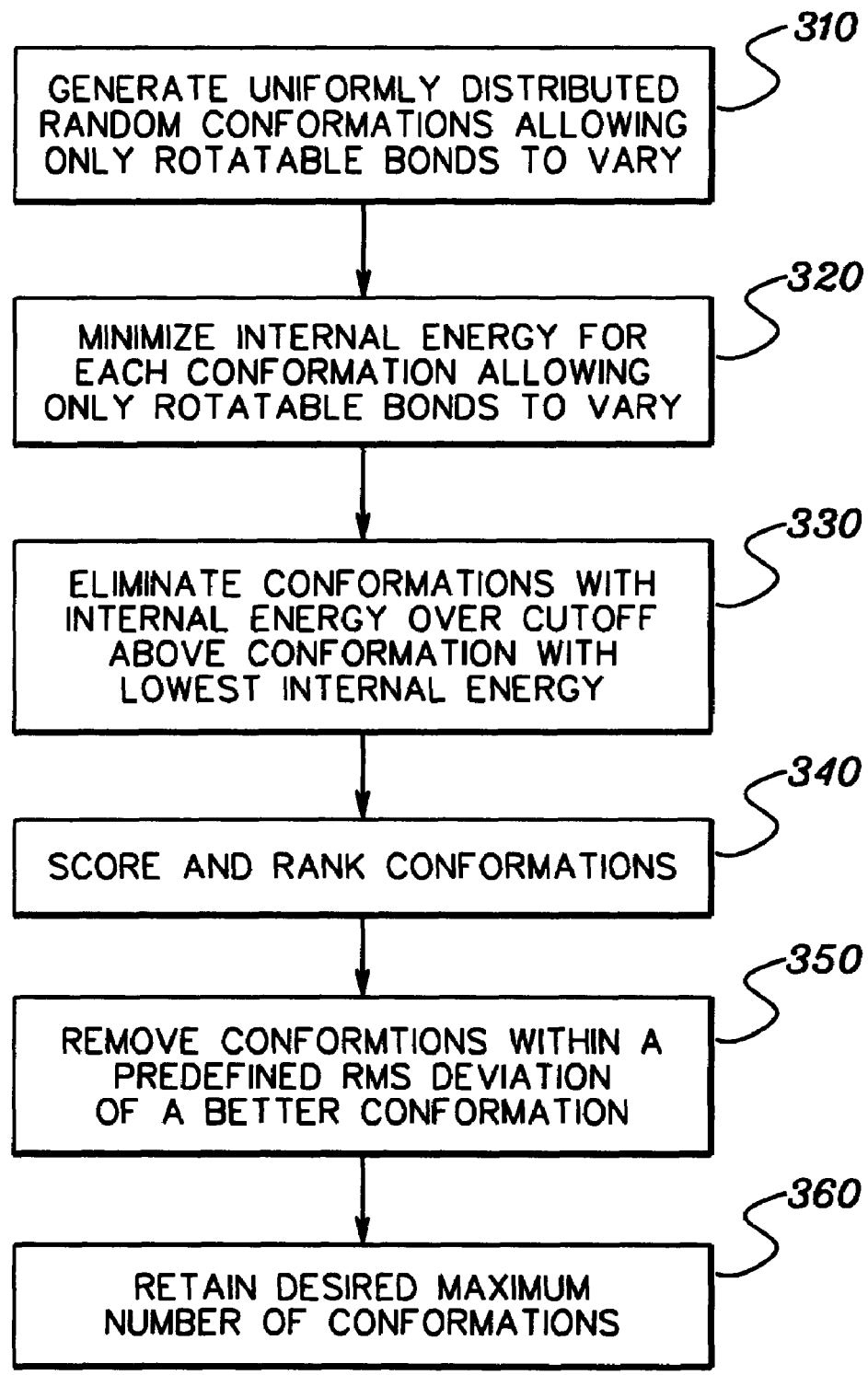
FIG. 3 is a flowchart of one embodiment of a molecular conformational search procedure which can be employed by the docking approach of FIG. 2, in accordance with the principles of the present invention.

Referring to FIG. 3, uniformly distributed random conformations are generated allowing only rotatable bonds to vary 310. For example, 1,000 uniformly distributed random conformations can be generated varying only the rotatable bonds. The internal energy of each conformation is then minimized, again allowing only rotatable bonds to vary 320. Internal energy can be estimated, for example, using van der Waals potentials and dihedral angle term, reference: Diller, D. J. and C. L. M. J. Verlinde "A Critical Evaluation of Several Global Optimization Algorithms for the Purpose of Molecular Docking," Journal of Computational Chemistry, 1999, Vol. 20(16), p. 1740–1751, which is hereby incorporated herein by reference in its entirety. Each conformation can be minimized using, for example, a BFGS (Broyden-Fletcher-Goldfarb-Shanno) optimization algorithm. The algorithm is an updating formula used to iteratively build up an approximation of the minimum of a function f. The formula has the form:

$$x_{i+1} = x_i - H_i \cdot \nabla f_i$$

$$H_i + 1 = H_i + \frac{(x_{i+1} - x_i) \otimes (x_{i+1} - x_i)}{(x_{i+1} - x_i) \cdot (\nabla f_{i+1} - \nabla f_i)} - \frac{[H_i \cdot (\nabla f_{i+1} - \nabla f_i)] \otimes [H_i \cdot (\nabla f_{i+1} - \nabla f_i)]}{(\nabla f_{i+1} - \nabla f_i) \cdot H_i \cdot (\nabla f_{i+1} - \nabla f_i)} + [(\nabla f_{i+1} - \nabla f_i) \cdot H_i \cdot (\nabla f_{i+1} - \nabla f_i)] u \otimes u$$

where u is defined as the vector $$u \equiv \frac{(x_{i+1} - x_i)}{(x_{i+1} - x_i) \cdot (\nabla f_{i+1} - \nabla f_i)} - \frac{H_i \cdot (\nabla f_{i+1} - \nabla f_i)}{(\nabla f_{i+1} - \nabla f_i) \cdot H_i \cdot (\nabla f_{i+1} - \nabla f_i)}$$

where $x_i$ is the vector of the initial position of the ligand;

$x_i$ is the vector of the initial position of the ligand;

$x_{i+1}$ is the updated vector of the position of the ligand;

$f_i$ is the function to be minimized, in this case, internal energy;

$\Delta f_i$ is the gradient, or second derivative, of the function;

$\Delta f_{i+1}$ is the updated gradient of the function;

$H_i$ is the ith approximation to the inverse of the Hessian matrix (second derivatives of f); and $H_{i+1}$ is the updated approximation to the inverse of the Hessian matrix.

Conformations with internal energy over a selected cutoff above a conformation with the lowest internal energy are eliminated 330. For example, any conformation with an internal energy of 15 kcal/mol above the conformation with the lowest internal energy is eliminated. The remaining conformations are scored and ranked 340. Conformations can be ranked by a score defined as:

$$\text{Score} = \text{Strain} - 0.1 \times \text{SASA}$$

where SASA is the "solvent accessible surface area" of a particular conformation; and "strain" of a given conformation of a given molecule is the internal energy of the given conformation minus the internal energy of the conformation of the given molecule with the lowest internal energy. Conformations within a pre-defined rms deviation of a better conformation are removed 350. For example, any conformation within an rms deviation of 1.0 Å of a higher ranked (i.e., better) conformation can be removed. This clustering is a means to remove redundant conformations. A maximum number of desired conformations, for example, 50 conformations, are retained at the end of the conformational analysis step 360.

If more than the desired number of conformations remain after clustering, then the lowest ranked conformations can be removed until the desired number of conformations remain.

The process of a small molecule binding to a protein target is a balance between "solvation" by water versus "solvation" by the protein. With this in mind, the solvent accessible surface area term can be chosen in analogy with simple aqueous salvation models, e.g., reference Eisenberg, D. and A. D. McLachlan, "Solvation Energy in Protein Folding and Binding," Nature, 1986, Vol. 319, p. 199–203; Ooi, T., et al., "Accessible Surface Areas as a Measure of the Thermodynamic Parameters of Hydration of Peptides," Proceedings of the National Academy of Sciences, 1987, Vol. 84, p. 3086–3090; and Vajda, S., et al., "Effect of Conformational Flexibility and Solvation on Receptor-ligand Binding Free Energies," Biochemistry, 1994, Vol. 33, p. 13977–13988, each of which is hereby incorporated herein by reference in its entirety. The key difference in protein versus water "solvation" is that water competes for polar interactions only, while a protein effectively competes for both polar and hydrophobic interactions. Therefore, for purposes of this invention, polar and apolar surface areas are treated identically. The choice of 0.1 as a weight for the surface area term is somewhat arbitrary, but is comparable to the weights chosen for surface area based solvation models. Ultimately, conformations with more solvent accessible surface area are going to be able to interact more extensively with a target protein and can, therefore, be of somewhat higher strain and still bind tightly. A more refined ranking system could be used with the present invention, but this approach to ranking conformations supplies reasonable conformations.

The Binding Site Image—Locating the Hot Spots

Figure 4:
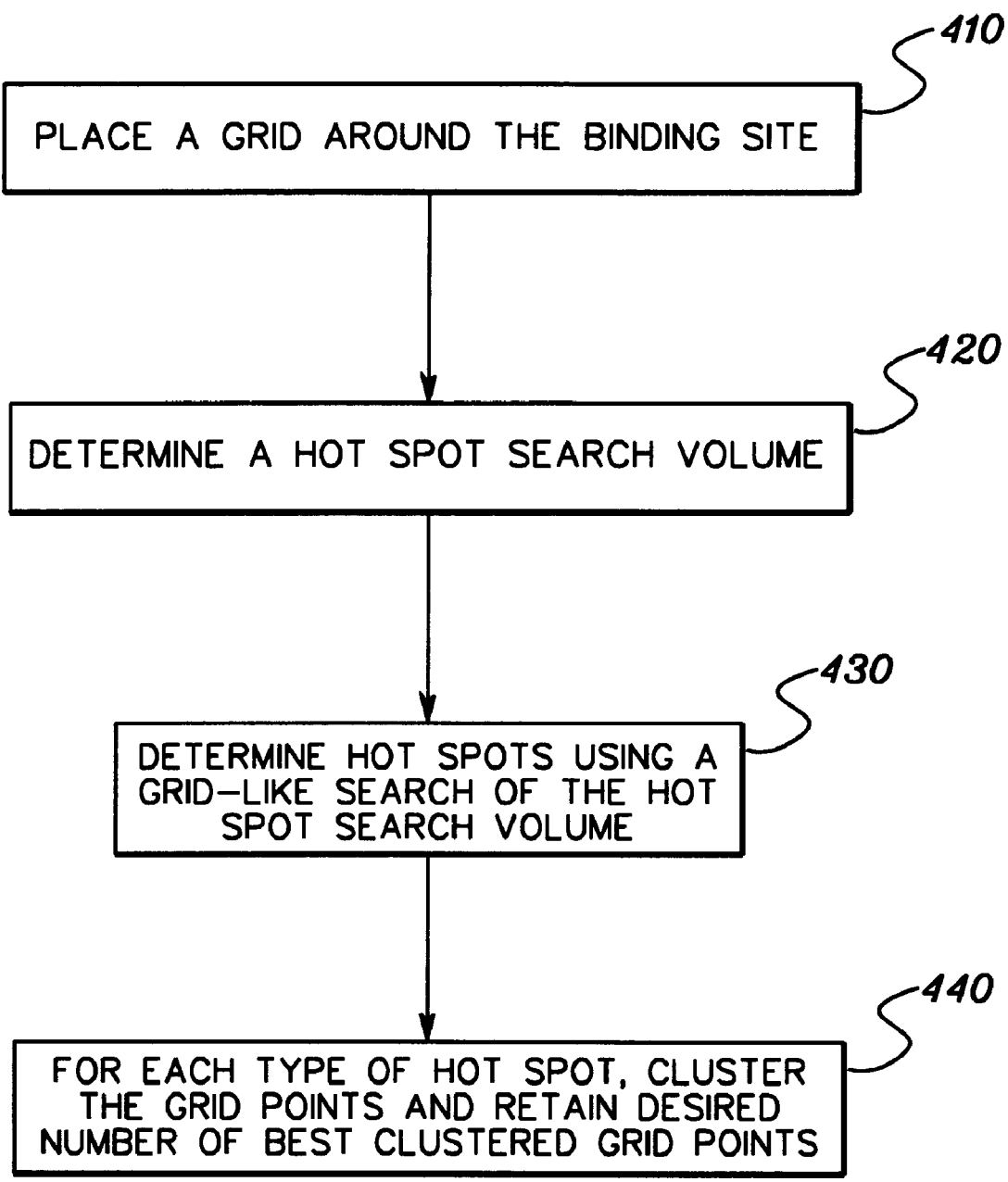
FIG. 4 is a flowchart of one embodiment of establishing a binding site image for use with the molecular docking approach of FIG. 2, in accordance with the principles of the present invention.

The binding site image comprises a list of apolar hot spots, i.e., points in the binding site that are favorable for an apolar atom to bind, and a list of polar hot spots, i.e., points in the binding site that are favorable for a hydrogen bond donor or acceptor to bind. One procedure for creating these two lists is depicted in FIG. 4. First, in order to find the binding site, a grid is placed around the binding site 410. By way of example, the grid may be at least 20 Å×20 Å×20 Å with at least 5 Å of extra space in each direction. A 0.2 Å spacing can be used for the grid. Next, a "hot spot search volume" is determined 420. This is accomplished by eliminating any grid point inside the protein. Any point contained in, for example, a 6.0 Å or larger sphere not touching the protein can also be eliminated. The largest remaining connected piece becomes the "hot spot search volume".

The hot spots can then be determined using a grid-like search of the hot spot search volume 430. By way of example, a grid-like search is described in Goodford, P. J., "A Computational Procedure for Determining Energetically Favorable Binding Sites on Biologically Important Macromolecules," Journal of Medicinal Chemistry, 1985, Vol. 28(7), p. 849–857, which is hereby incorporated herein by reference in its entirety. To find the apolar hot spots, an apolar probe is placed at each grid point in the hot spot search volume, the probe score is calculated and stored. The process is repeated for polar hot spots. For each type of hot spot, the grid points are clustered and a desired number of best clustered grid points is maintained 440. For example, the top 30 clustered grid points may be retained.

The Matching Procedure—Forming an Initial Complex

Figure 5:
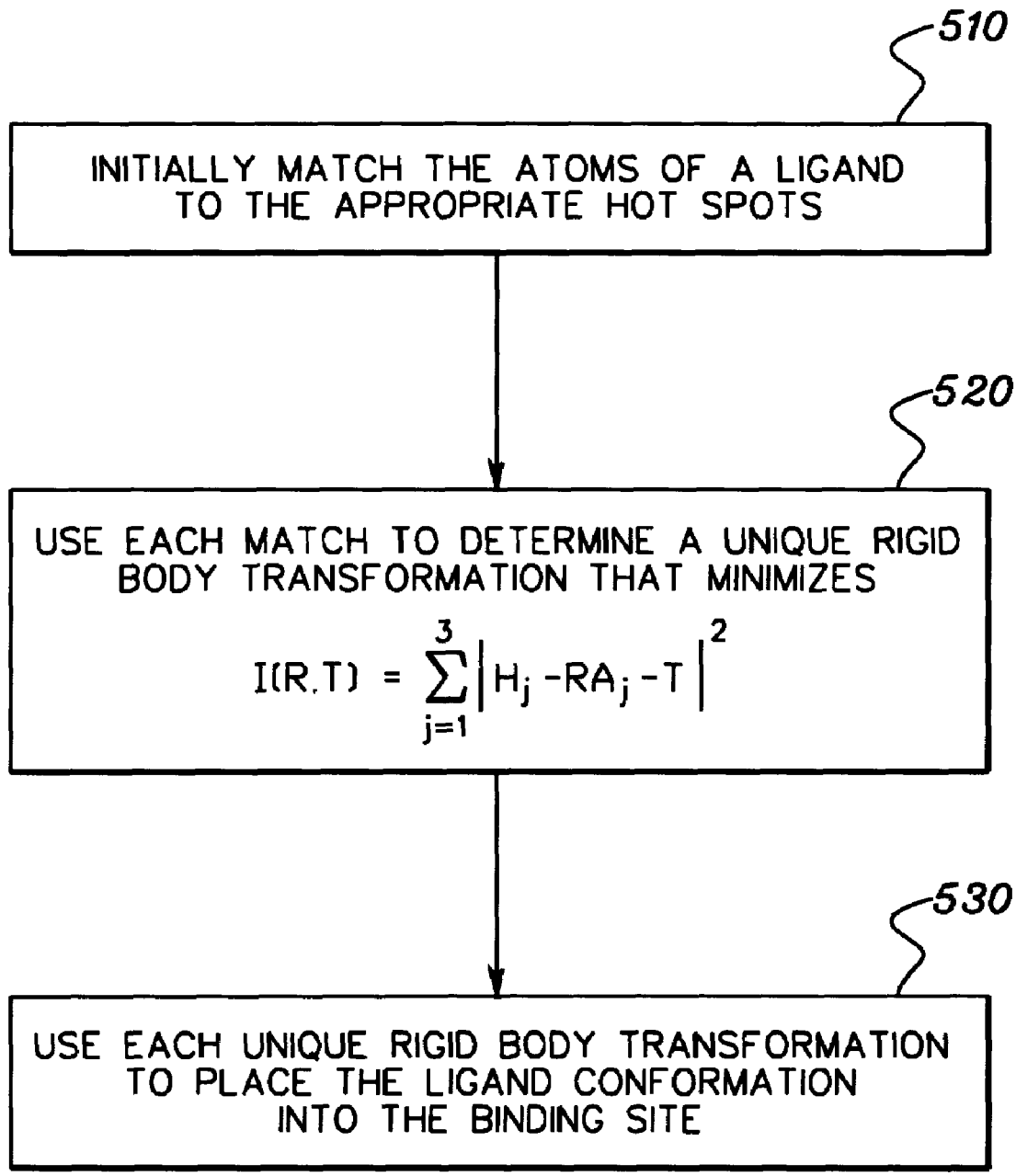
FIG. 5 is a flowchart of one embodiment of a matching procedure for use with the molecular docking approach of FIG. 2, in accordance with the principles of the present invention.

Referring to FIG. 5, in order to initially position a given conformation of a ligand as a rigid body into the binding site, the atoms of the ligand are matched to the appropriate hot spots 510. More precisely, in one example, a triplet of atoms, $A_1, A_2, A_3$ is considered a match to a triplet of hot spots, $H_1, H_2, H_3$ if:

i. The type of $A_j$ matches the type of $H_j$ for each j=1,2,3, that is, apolar hot spots match apolar atoms and polar hot spots match polar atoms.

ii. $D(A_j, A_k) = D(H_j, H_k) \pm \delta$ for all j,k=1,2,3 where $D(A_j, A_k)$ and $D(H_j, H_k)$ are the distance from $A_j$ to $A_k$ and $H_j$ to $H_k$, respectively, and $\delta$ is some allowable amount of error, e.g., between 0.25 Å and 0.5 Å.

To restate, a match occurs, in one example, when three hot spots forming a triangle and three atoms of the ligand forming a triangle substantially match. That is, a match occurs when the triangles are sufficiently similar with the vertices of each triangle being the same type and the corresponding edges of similar length. The matching algorithm finds all matches between atoms of a given conformation and the hot spots. Each match then determines a unique rigid body transformation. The rigid body transformation is then used to bring the conformation into the binding site to form the initial protein-ligand complex.

In step 520, each match determines a unique rigid body transformation that minimizes $$I(R, T) = \sum_{j=1}^{3} |H_j - RA_j - T|^2$$

where R is, for instance, a 3×3 rotation matrix and T is a translation vector. Again, a rigid body transformation comprises in one example, a 3×3 rotation matrix, R, and translation vector T, so that points X (the position of an atom of the conformation) are transformed by RX+T. Each rigid body transformation, which can be determined analytically, is then used to place the ligand conformation into the binding site 530. For this aspect of the calculation, several algorithms for finding all matches were tested. The geometric hashing algorithm developed for FlexX (see: Rarey, M., S. Welfing, and T. Lengauer, "Placement of Medium-sized Molecular Fragments Into Active Sites of Proteins," Journal of Computer-Aided Molecular Design, 1996, Vol. 10, p. 41–54, which is hereby incorporated herein by reference in its entirety), proved to be the most efficient.

Optimization Stage

Figure 6:
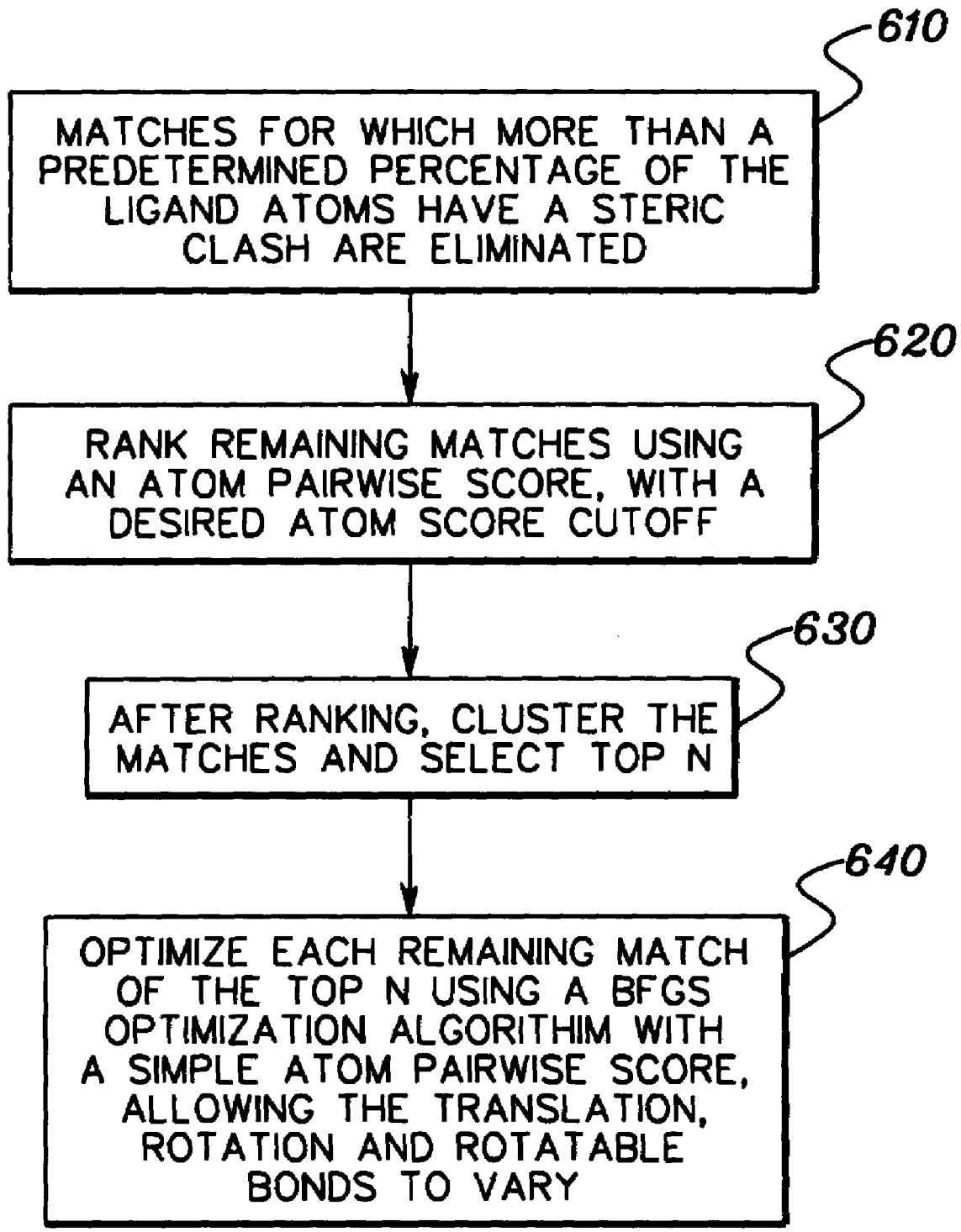
FIG. 6 is a flowchart of one embodiment of an optimization stage for optimizing ligand positions within identified matches for use with the molecular docking approach of FIG. 2, in accordance with the principles of the present invention.

A single conformation can produce up to 10,000 matches. In the interest of efficiency, most of these matches cannot be optimized, so a pruning/scoring strategy is desired. FIG. 6 depicts one such strategy.

Referring to FIG. 6, initially all matches for which more than a predetermined percentage (e.g., 10%) of the ligand atoms have a steric clash can be eliminated 610. The remaining matches are ranked using an atom pairwise score described below, with an atom score cutoff of for example 1.0 620. Use of a cutoff allows matches that fit reasonably well with a few steric clashes to survive to the final round, and the choice of 1.0 is merely exemplary. After being ranked, the matches are clustered, and the top N matches are selected to move into the final stage 630, where N may comprise, for instance, a number in the range of 25–100.

Each remaining match is optimized using BFGS optimization algorithm as described above, wherein a simple atom pairwise score is the function which is minimized 640. In one embodiment, the score can be modeled after the Piecewise Linear Potential (see, Gehlhaar, D. K., et al., "Molecular Recognition of The Inhibitor AG-1343 By HIV-1 Protease: Conformationally Flexible Docking by Evolutionary Programming," Chemistry & Biology, 1995, Vol. 2, p. 317–324, which is hereby incorporated herein by reference in its entirety) with a difference being that the score used herein is preferably differentiable. For this score, all hydrogens are ignored, and all non-hydrogen atoms are classified into one of four categories:

i. Apolar—anything that cannot form a hydrogen bond.
    ii. Acceptor—any atom that can act as a hydrogen bond acceptor, but not as a donor.
    iii. Donor—any atom that can act as a hydrogen bond donor, but not as an acceptor.
    iv. Donor/Acceptor—any atom that can act as both a hydrogen bond donor and an acceptor.

Figure 7:
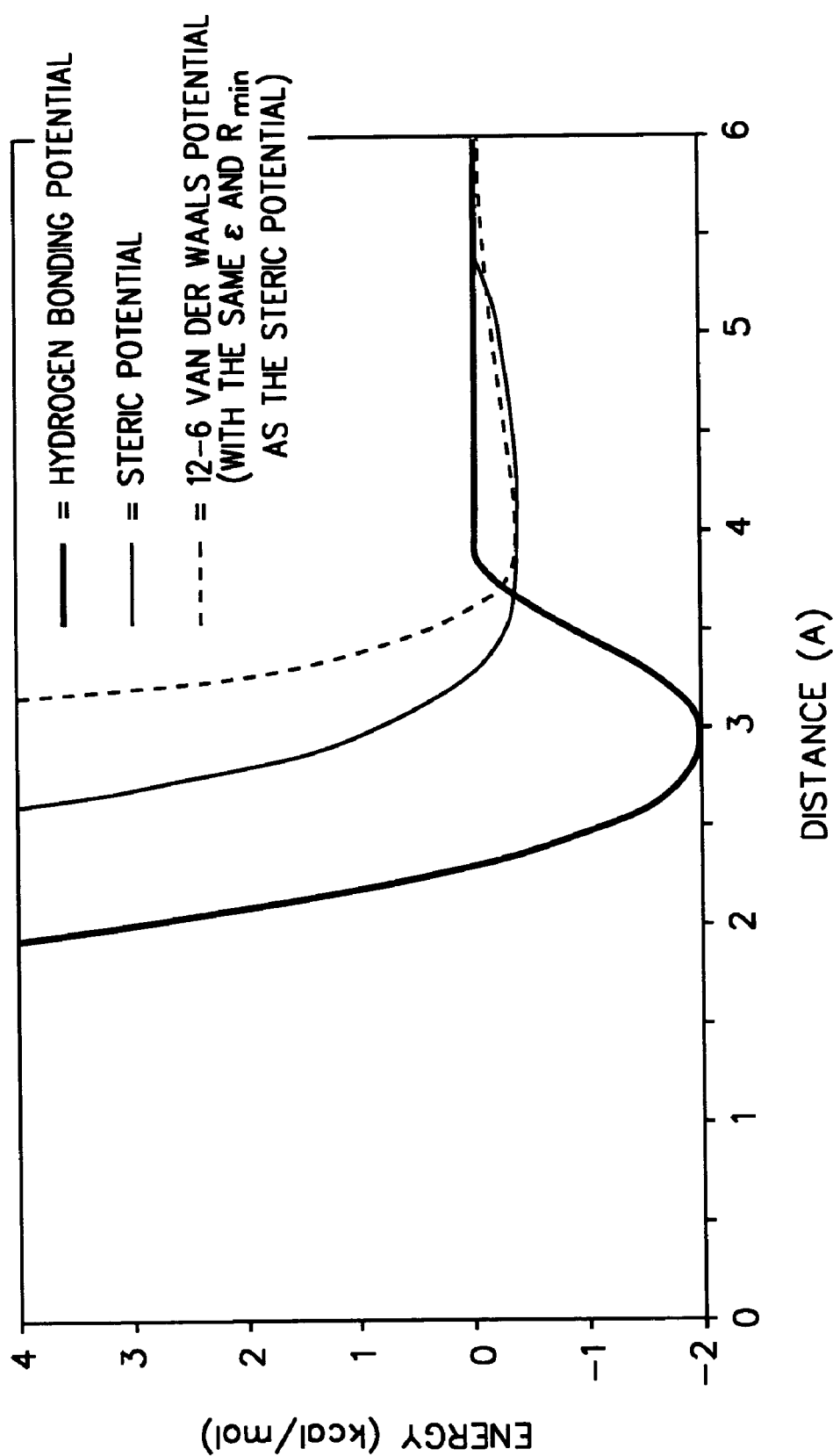
FIG. 7 graphically depicts a hydrogen bonding potential and a steric potential for use in atom pairwise scoring in accordance with the principles of the present invention.

The score between two atoms is calculated using either a hydrogen bonding potential or a steric potential. The two potentials, shown in FIG. 7, have the mathematical form $$F(r) = \varepsilon \left[ \left( \frac{(1+\sigma)R_{min}^2}{r^2 + \sigma R_{min}^2} \right)^6 - 2\left( \frac{(1+\sigma)R_{min}^2}{r^2 + \sigma R_{min}^2} \right)^3 \right] \Phi(r^2 : r_1^2, r_0^2)$$

where $R_{min}$ is the position of the score minimum, $\varepsilon$ is the depth of the minimum, $\sigma$ is a softening factor, and $\Phi(r:r_1, r_0)$ is a differentiable cutoff function of r (the distance between the pair of atoms) having the properties that when $r<r_1 \Phi=1$ and when $r>r_0 \Phi=0$. Each potential, steric and hydrogen bonding, is assigned its own set of parameters. The parameters for these potentials can be chosen by one skilled in the art via intuition and subsequent testing, but they do not need to be fully optimized. Table 2 contains example parameters for the pairwise potentials.

TABLE 2

|  | hydrogen bonding potential | Steric Potential |
|---|---|---|
| $\varepsilon$ | 2.0 | 0.4 |
| $\sigma$ | 0.5 | 1.5 |
| $R_{min}$ | 3.0Å | 4.05Å |
| $r_1$ | 3.0Å | 5.0Å |
| $r_0$ | 4.0Å | 6.0Å |

These potentials are very similar to the 12-6 van der Waals potentials used in many force fields with two differences. First, the softening factor, $\sigma$, makes the potentials significantly softer than the typical 12-6 van der Waals potentials (see FIG. 7), i.e., mild steric clashes common in docking runs are tolerated by this potential. In spirit, the softening factor implicitly models small induced fit effects of the protein which can be important (see, Murray, C. W., C. A. Baxter, and D. Frenkel, "The Sensitivity of The Results of Molecular Docking to Induced Fit Effects: Application to Thrombin, Thermolysin and Neuramimidase," Journal of Computer-Aided Molecular Design, 1999, Vol. 12, p. 547–562, which is hereby incorporated herein by reference in its entirety), and in practice, makes the potential much more error tolerant. The second difference is the cutoff function. This function guarantees that the potential is zero beyond a finite distance usually between 5.0 Å and 6.0 Å. This along with some organization of the protein atoms significantly speeds up the direct calculation of the score.

An attempt was made to calculate the scores both directly and through precalculated grids. The advantage of using the grids is that the score can be calculated very rapidly. Grids were found to be 5–10 times faster than the direct calculation. The advantage of the direct calculation is that effects, such as protein flexibility and solvent mobility, can be accommodated more easily. Since using the grids did not seem to cause any deterioration in the quality of the docking results and since protein flexibility or solvent mobility is currently not included, for the results presented hereinbelow, the scores were calculated through precalculated grids. For the purpose of the BFGS optimization algorithm, all derivatives were calculated analytically including those with respect to the rotatable bonds (see, Haug, E. J. and M. K. McCullough, "A Variational-Vector Calculus Approach to Machine Dynamics," Journal of Mechanisms, Transmissions, and Automation in Design, 1986, Vol. 108, p. 25–30, which is hereby incorporated herein by reference in its entirety).

Test Results

To test the docking procedure, the GOLD test set was used (see Jones, G., et al., "Development and Validation of a Generic Algorithm for Flexible Docking," Journal of Molecular Biology, 1997, Vol. 267, p. 727–748, which is hereby incorporated herein by reference in its entirety). For the test set, "protein-ligand complexes were selected from the Protein Data Bank (Bernstein *J. Mol. Biol.*, 112, 535–542 (1977)). These complexes were selected on the basis or pharmacological interest and whether the ligands involved were 'drug-like'." (Jones, J. Mol. Biol. 267, 728 (1997) Any covalently bound ligand or any ligand bound to a metal ion was removed because it cannot, at present, be modeled by the scoring function described herein. In addition, any "surface sugars" were removed as they are not typical of the problems encountered. This left a total of 103 cases (see Table 1 below). No further individual processing of the test cases was performed. (Note that the "Protein Data Bank" (PDB) is a database where target molecule structures are placed. The "PDB Code" is a four letter code that allows a given structure to be found and extracted from the PDB.)

TABLE 1

| PDB Code | Number of Rot Bonds | Minimum RMSD | RMSD of Top Score |
|---|---|---|---|
| 1aaq | 17 | 1.35 | 1.4 |
| 1abe | 0 | 0.31 | 0.31 |
| 1acj | 0 | 0.59 | 0.71 |
| 1ack | 2 | 0.45 | 0.46 |
| 1acm | 6 | 0.31 | 0.31 |
| 1aha | 0 | 0.25 | 0.53 |
| 1apt | 18 | 1.10 | 1.63 |
| 1atl | 9 | 1.05 | 4.24 |
| 1azm | 1 | 1.40 | 2.33 |
| 1baf | 7 | 0.76 | 7.10 |
| 1bbp | 11 | 1.45 | 1.55 |
| 1cbs | 5 | 0.70 | 12.63 |

TABLE 1-continued

| PDB Code | Number of Rot Bonds | Minimum RMSD | RMSD of Top Score |
|---|---|---|---|
| 1cbx | 5 | 0.53 | 2.30 |
| 1cil | 3 | 1.07 | 5.94 |
| 1com | 3 | 0.76 | 0.76 |
| 1coy | 0 | 0.52 | 0.70 |
| 1cps | 5 | 0.85 | 0.97 |
| 1dbb | 1 | 0.72 | 0.85 |
| 1dbj | 0 | 0.64 | 5.90 |
| 1did | 2 | 2.76 | 3.65 |
| 1die | 1 | 2.24 | 2.30 |
| 1drl | 2 | 1.02 | 1.61 |
| 1dwd | 9 | 0.75 | 7.98 |
| 1eap | 10 | 0.79 | 3.95 |
| 1eed | 19 | 3.41 | 3.41 |
| 1epb | 5 | 0.75 | 2.86 |
| 1eta | 5 | 5.48 | 7.29 |
| 1etr | 9 | 2.70 | 7.06 |
| 1fen | 4 | 0.98 | 2.45 |
| 1fkg | 10 | 1.68 | 1.72 |
| 1fki | 0 | 0.30 | 0.54 |
| 1frp | 6 | 0.67 | 1.13 |
| 1ghb | 4 | 0.90 | 0.94 |
| 1glp | 10 | 1.45 | 8.92 |
| 1glq | 13 | 1.91 | 9.96 |
| 1hdc | 6 | 1.52 | 11.25 |
| 1hef | 19 | 3.63 | 5.29 |
| 1hfc | 10 | 1.37 | 7.77 |
| 1hri | 9 | 1.49 | 3.29 |
| 1hsl | 3 | 0.76 | 2.21 |
| 1hyt | 5 | 0.79 | 1.56 |
| 1icn | 15 | 1.78 | 9.43 |
| 1ida | 15 | 1.32 | 1.38 |
| 1igj | 3 | 0.90 | 7.46 |
| 1imb | 2 | 1.64 | 4.48 |
| 1ive | 2 | 2.55 | 6.63 |
| 1lah | 4 | 0.71 | 0.77 |
| 1lcp | 3 | 0.53 | 4.65 |
| 1ldm | 1 | 0.80 | 5.24 |
| 1lic | 15 | 1.32 | 4.39 |
| 1lmo | 6 | 5.00 | 8.40 |
| 1lna | 6 | 1.35 | 1.46 |
| 1lst | 5 | 0.58 | 1.43 |
| 1mcr | 5 | 3.92 | 5.41 |
| 1mdr | 2 | 0.41 | 0.78 |
| 1mmq | 7 | 0.55 | 0.60 |
| 1mrg | 0 | 0.45 | 3.42 |
| 1mrk | 2 | 0.94 | 2.91 |
| 1mup | 2 | 1.74 | 4.40 |
| 1nco | 8 | 2.88 | 8.50 |
| 1pbd | 1 | 0.29 | 0.38 |
| 1poc | 23 | 2.81 | 8.62 |
| 1rne | 21 | 8.83 | 10.14 |
| 1rob | 4 | 0.83 | 1.17 |
| 1snc | 5 | 1.17 | 5.60 |
| 1srj | 3 | 0.48 | 0.58 |
| 1stp | 5 | 0.33 | 0.48 |
| 1tdb | 4 | 1.33 | 7.09 |
| 1tka | 8 | 1.44 | 1.44 |
| 1tng | 1 | 0.35 | 0.42 |
| 1tnl | 1 | 0.45 | 4.25 |
| 1tph | 3 | 0.63 | 1.44 |
| 1ukz | 4 | 0.43 | 6.20 |
| 1ulb | 0 | 1.22 | 4.19 |
| 1wap | 3 | 0.29 | 0.34 |
| 1xid | 2 | 0.79 | 4.23 |
| 1xie | 1 | 0.34 | 3.89 |
| 2ada | 2 | 0.53 | 0.58 |
| 2ak3 | 4 | 1.91 | 3.24 |
| 2cgr | 7 | 0.61 | 3.46 |
| 2cht | 2 | 0.18 | 0.40 |
| 2cmd | 5 | 0.50 | 2.36 |
| 2ctc | 3 | 0.36 | 4.15 |
| 2dbl | 6 | 0.40 | 0.96 |
| 2gbp | 1 | 0.17 | 0.17 |
| 2lgs | 4 | 0.71 | 5.48 |
| 2phh | 1 | 0.51 | 0.51 |
| 2plv | 5 | 1.98 | 7.40 |
| 2r07 | 15 | 1.17 | 2.45 |
| 2sim | 8 | 0.92 | 1.37 |
| 2yhx | 3 | 1.07 | 6.99 |
| 3aah | 3 | 0.48 | 0.68 |
| 3cpa | 5 | 0.92 | 1.40 |
| 3hvt | 1 | 0.27 | 0.56 |
| 3ptb | 0 | 0.22 | 0.28 |
| 3tpi | 6 | 0.42 | 0.53 |
| 4cts | 3 | 0.73 | 0.77 |
| 4dfr | 9 | 2.05 | 8.72 |
| 4fab | 2 | 2.52 | 4.45 |
| 4phv | 12 | 0.38 | 0.38 |
| 6abp | 0 | 0.34 | 0.34 |
| 7tim | 3 | 0.40 | 0.98 |
| 8gch | 7 | 1.70 | 4.45 |

As expected, the rms deviation between the bound conformation (X=ray) and the closest computationally generated conformation increases with the number of rotatable bonds. In all but 5 cases, at least one conformation was generated by the conformational search with 1.5 Å rms deviation of the bound conformation. The most interesting aspect of the conformational search results is that for some of the more rigid ligands, the minimum rms deviation was large. For example, there are several ligands with fewer than five rotatable bonds, but with a minimum rms deviation near 1.0 Å. This occurs for two reasons. First, clustering radius of 1.0 Å in all cases was used. This prevented the conformational space of small ligands from being sufficiently sampled. However, it is within the scope of the present invention that a clustering radius dependent on the molecule size could be used to alleviate this particular problem. The second problem is that a bond between two $sp^2$ atoms was always treated as being conjugated. Thus, whenever this type of bond is encountered, it is strongly restrained to be planar. While bonds between two $sp^2$ atoms are often conjugated, this is clearly an over-simplification. This may be addressed, in accordance with the invention by allowing the dihedral angles between two $sp^2$ atoms to deviate from planarity. This deviation can then be penalized according to the degree of conjugation. The penalty could be chosen crudely based on the types of the $sp^2$ atoms (see, S. L. Mayo, B. D. Olafson, & W. A. Goddard, "DRIEDING: A Generic Force Field for Molecular Simulations", J. Phys. Chem. 1990, Vol. 94, p. 8897).

The Docking Results

For the docking runs, two different sets of parameters were tested to see their effects on the quality and speed of the docking runs: one for high quality docking and one for rapid searches. The key difference between the two sets of parameters are the match tolerance and the number and length of the BFGS optimization runs. The match tolerance ranges from 0.5 Å for the high quality to 0.25 Å for the rapid searches. Note that the larger tolerance the more matches will be found. Thus, a larger tolerance means a more thorough search, while a smaller tolerance denotes a less thorough but faster search. For the high quality runs, a maximum of 100 matches per ligand were optimized for 100 steps compared to 25 matches per ligand for 20 steps for the rapid searches.

The first problem is to generate at least one docked position between a given rms deviation cutoff. Here, terminology is adopted that a ligand that is docked to within X Å of the crystallographically observed position of the ligand is referred to as an X Å hit. The rms deviations are shown for the high quality runs in Table 1. For the high quality runs, 89 of the 103 cases produce at least one 2.0 Å hit. The numbers drop to 80 at 1.5 Å, 63 at 1.0 Å and 26 at 0.5 Å. For the rapid searches, 75 of the 103 cases produce a 2.0 Å hit, 65 produce a 1.5 Å hit, 42 produce a 1.0 Å hit and 16 produce a 0.5 Å hit. In both cases, these numbers compare favorably with similar statistics from other docking packages that have been tested on the Gold or similar test sets (see, Jones, G., et al., Development and Validation of a Generic Algorithm for Flexible Docking," Journal of Molecular Biology, 1997, Vol. 267, p. 727–748; Baxter, C. A. et al., "Flexible Docking Using Tabu Search and an Empirical Estimate of Binding Affinity," PROTEINS: Structure, Function, and Genetics, 1998, Vol. 1998, p. 367–382; Rarey, M., B. Kramer, and T. Lengauer, "The Particle Concept: Placing Discrete Water Molecules During Protein-ligand Docking Predictions," PROTEINS: Structure, Function, and Genetics, 1999, Vol. 34, p. 17–28; Rarey M., B. Kramer, and T. Lengauer, "Docking of Hydrophobic Ligands With Interaction-based Matching Algorithms," Bioinformatics, 1999, Vol. 15(3), p. 243–250; and Kramer, B., M. Rarey, and T. Lengaeur, "Evaluation of the FlexX Incremental Construction Algorithm for Protein-Ligand Docking," PROTEINS: Structure, Function, and Genetics, 1999, Vol. 37, p. 228–241).

The second problem is to correctly rank the docked compounds, i.e., is the top ranked conformation reasonably close to the crystallographically observed position for the ligand. This is a significantly more difficult problem than the first. The rms deviation between the top scoring docked position and the observed position for the high quality runs are given in Table 1. In this case, there is little difference between the two sets of parameters. For the high quality runs, 48 of the 103 cases produce a 2.0 Å hit as the top scoring docked position. This number drops to 41 at 1.5 Å, 34 at 1.0 Å and 10 at 0.5 Å. For the rapid searches, 45 of the 103 cases produce a 2.0 Å hit as the top scoring docked position with 41 at 1.5 Å, 34 at 1.0 Å and 10 at 0.5 Å.

The utility of the scoring function used in this study lies less as a tool to absolutely rank the docked conformations than as an initial filter to select only a few docked conformations. Most of the well docked positions, i.e., low rms deviations, survive this 10% cutoff. Most of the docked positions, however, do not. For the high quality runs, on average 74 positions are found, but after the 10% cutoff on average only 8 remain. For the rapid searches, on average nearly 21 positions are found, but after the cutoff on average only 5 remain. At this point, the docked positions that survive the 10% score cutoff could be further optimized, visually screened, or passed to a more accurate, but less efficient scoring function.

For the high quality runs, the average CPU time (e.g., using a Silicon Graphics Incorporated (SGI) computer R12000) per test case is approximately 4.5 seconds. At this rate, screening one million compounds with one CPU would take about 50 days. For the rapid searches, the average CPU time per test case drops to approximately 1.1 seconds per test case. At this rate, screening one million compounds with one CPU would take about 12 days. Because database docking is a highly parallel job, multiple CPUs could easily cut this to a reasonable amount of time (for example, a day or so).

Some Specific Successful Cases

In this section, a few of the successful cases are shown to demonstrate the strengths of the approach described herein to docking small molecules. In all of these cases, the results shown are from the medium quality docking runs. The first case is the dipeptide Ile-Val from the PDB entry 3tpi (see, Marquart, M., et al., "The Geometry of the Reactive Site and of the Peptide Groups in Trypsin, Trypsinogen and Its Complexes With Inhibitors," Acta Crystallographica, 1983, Vol. B39, p. 480, which is hereby incorporated herein by reference in its entirety). This case has no clear anchor fragment and as a result, the incremental construction approach to docking might have difficulties with this ligand. Our conformational search procedure produced a conformation within 0.42 Å of the observed conformation. The rms deviation between the best scoring docked position and the observed position is 0.53 Å.

The second example, with a ligand having 15 rotatable bonds, is a much more difficult example. It is an HIV protease inhibitor from the PDB entry lida (see, Tong, L., et al., "Crystal Structures of HIV-2 Protease In Complex With Inhibitors Containing Hydroxyethylamine Dipeptide Isostere," Structure, 1995, Vol. 3(1), p. 33–40, which is hereby incorporated herein by reference in its entirety). In this case the conformational search procedure was able to generate a conformation with an rms deviation of 0.96 Å from the bound conformation. The rms deviation for the top scoring docked position is 1.38 Å. In fact, the top 13 scoring docked positions are all within 2.0 Å of the observed position with the closest near 1.32 Å.

The final case is an HIV protease inhibitor from the PDB entry 4phv (see, Bone, R., et al., "X-ray Crystal Structure of The HIV Protease Complex With L-700, 417, An Inhibitor With Pseudo C2 Symmetry," Journal of the American Chemical Society, 1991, Vol. 113 (24), p. 9382–9384, which is hereby incorporated herein by reference in it entirety). The ligand in this case has 12 rotatable bonds. This clearly demonstrates the value of including the final flexible gradient optimization step of the ligand. The closest conformation produced from the conformational search procedure is 1.32 Å from the crystallographically observed conformation. With an rms deviation of 0.38 Å, the top scoring docked position is also the closest to the observed position. The smallest rms deviation that could have been obtained without the flexible optimization is that of the closest conformation generated by the conformational search procedure, i.e., 1.32 Å. Thus, in this case, the flexible optimization decreased the final rms deviation by at least 1.0 Å.

An Analysis of the Errors and Avenues for Improvement

It is often assumed that when docking simulation fails, the score has failed, i.e., the global minimum of the scoring function did not correspond to the crystallographically determined position for the ligand. Since the docking problem involves many degrees of freedom, it is reasonable to believe that in many cases the failure can be attributed to insufficient search. It is the goal of this section to identify the cause of failure in the cases in which the procedure described herein performed poorly.

To classify docking failures as either scoring failures or search failures, the ligand was taken as bound to the protein and a BFGS optimization was performed. If the resulting score was significantly less than the best score found from the docking runs, the failure is classified as a search failure. Every other failure is classified as a scoring failure.

The vast majority of the cases qualify as moderate scoring errors, i.e., the global minimum appears not to correspond to the crystallographic position of the ligand, but the percent difference between the global minimum and the best score near the crystallographic position of the ligand is less than 10%. In these cases, it is difficult to decide which aspects of the score are failing, but it is reasonable to believe that many of these cases can be corrected simply by including some more detail in the scoring function, such as angular constraints on the hydrogen bonding term or a solvation model. There are, however, a few cases with dramatic scoring errors. These cases provide some insight into the weakness of the score and the complexities of protein/ligand interactions.

The case 1glq (see, Garcia-Saez, I., et al., "Molecular Structure at 1.8 A of Mouse Liver Class pi Glutathione S-Transferase Complexed With S-(p-Nitrobenzyl) Glutathione and Other Inhibitors," Journal of Molecular Biology, 1994, Vol. 237, p. 298–314) pointed out the main weakness of the score used in this study—hydrogen bonding patterns. This is a polar ligand. The top ranked position for this ligand scores very well largely because there are many "perceived" hydrogen bonds. In reality, these hydrogen bonds would be extremely weak because the angular dependence of the interaction is poor. Moreover, the sulfur atom in the X-ray position is accepting a hydrogen bond from the OH of a tyrosine and the carboxylic acid is involved in a salt bridge with a lysine. Neither of these interactions was recognized by the scoring function described herein.

In the case 1ive (see, Jedrzejas, M. J., et al., "Structures of Aromatic Inhibitors of Influenza Virus Neuramimidase," Biochemistry, 1995, Vol. 34, p. 3144–3151), the correct position receives a relatively poor score largely due to the estimated strain of the observed conformation. The present invention recognizes certain bonds as being conjugated. Thus, a stiff penalty is applied when these bonds are not planar. In the observed conformation, the dihedral angles are all nearly 80° from planar. If these dihedral angles are forced to be near 0°, the conformation is no longer compatible with the observed interactions between the ligand and the protein. It would be difficult for any docking algorithm to predict these values for the dihedral angles.

The case 1hef (see, Murthy, K. H. M., et al., The Crystal Structures at 2.2-A Resolution of Hydroxyethylene-Based Inhibitors Bound to Human Immunodeficiency Virus Type 1 Protease Show That The Inhibitors are Present in Two Distinct Orientations," Journal of Biological Chemistry, 1992, Vol. 267, p. 22770–22778), an HIV protease inhibitor, is perhaps the most interesting of all of the dramatic scoring errors. The binding pocket is at the interface of a dimer with the protein monomers being related through a crystallographic symmetry operation. At the C-terminus of the ligand, a methyl group is within 2.0 Å. These interactions would be extremely difficult to predict. Our program did come up with an interesting alternate conformation for the C-terminus of the ligand. This conformation eliminates both the internal and external steric clashes and forms an additional hydrogen bond with the protein.

There are two cases that can be classified as conformational search failures: 1hef and 1poc. In these cases the best conformation produced is 2.1 Å and 2.3 Å, respectively. The ligand in the case 1poc has 23 rotatable bonds, and thus, it is very difficult to fully cover its conformational space with only 50 conformers. While the ligand in the case 1hef is also very flexible (18 rotatable bonds), the observed conformation, as described above, also has a serious steric clash. Thus, this is, as should be expected, a very difficult challenge for any conformational search procedure.

CONCLUSIONS

In this application, a new rapid technique for docking flexible ligands into the binding sites of proteins is presented. The method is based on a pre-generated set of conformations for the ligand and a final flexible gradient based optimization of the ligand in the binding site of the protein. Based on the results, this is a robust approach to handling ligand flexibility. With relatively few conformations (less than 50 per molecule), usually a conformation within 1.5 Å of the bound conformation can be generated. Applying the flexible optimization as the final step reduces the number of conformations required while maintaining high quality final docked positions.

There are opportunities to improve the exemplified docking technique. Such improvements also fall within the scope of the present invention. For example, the conformer generation, while reasonably successful, should treat small relatively rigid molecules and large flexible molecules differently. Since the conformational space of very large flexible molecules is too large to explore thoroughly, a Monte Carlo search algorithm is used. In addition, the score used to rank the conformations is certainly simplistic and can be improved. For example, variations of solvation models (see, Eisenberg, D. and A. D. McLachlan, "Solvation Energy in Protein Folding and Binding," Nature, 1986, Vol. 319, p. 199–203; Still, W. C., et al., "Semianalytical Treatment of Solvation For Molecular Mechanics and Dynamics," Journal of the American Chemical Society, 1990, Vol. 112, p. 6127–6129, both of which are hereby incorporated herein by reference in their entirety) would likely give better conformations. Finally, a better treatment of strain, particularly that for rotation about bonds between two $sp^2$ atoms, might lead to improved results.

In the embodiment exemplified, the algorithm used to find the polar hot spots tends to find any hydrogen bond donor and acceptor rather than those buried in the binding site. Improving the hot spot search routine will not only increase the quality of the technique, but will also decrease the number of hot spots needed and, thus, make the technique more efficient. Some available programs, such as GRID (see, Goodford, P. J., "A Computational Procedure for Determining Energetically Favorable Binding Sites on Biologically Important Macromolecules," Journal of Medicinal Chemistry, 1985, Vol. 28(7), p. 849–857; and Still, W. C., et al., "Semianalytical Treatment of Solvation For Molecular Mechanics and Dynamics," Journal of the American Chemical Society, 1990, Vol. 112, p. 6127–6129, both of which are hereby incorporated herein by reference in their entirety) or the LUDI binding site description (see, Bohm, H. J., "LUDI: Rule-based Automatic Design of New Substituents For Enzyme Inhibitor Leads," Journal of Computer-Aided Molecular Design, 1992," Vol. 6, p. 693–606, which is hereby incorporated herein by reference in its entirety) or a documented method (see, Mills, J. E. J., T. D. J. Perkins, and P. M. Dean, "An Automated Method For Predicting The Positions of Hydrogen-bonding Atoms In Binding Sites," Journal of Computer-Aided Molecular Designs, 1997, Vol. 11, p. 229–242, which is hereby incorporated herein by reference in its entirety) would likely show some improvement. In addition, separating the polar hot spots into donor, acceptor, ionic, etc., hot spots might improve the results. Finally, in a practical application, most users would be willing to spend some time to enhance the image, i.e., eliminate by hand bad hot spots, and add hot spots where needed. In practice, this will significantly improve docking runs.

In all docking programs, a good score should be efficient, error tolerant, and accurate. The score used here satisfies the first two qualities. These two qualities, however, are usually not compatible with the third. It appears that this score will still be useful as an initial screen after which a more accurate score can be applied. Geometric constraints for the hydrogen bonding term, recognition of ionic interactions and salvation effects, and terms for dealing with metals can be introduced to improve accuracy.

Nonetheless, when a crystal structure is available, the approach of the present invention to molecular docking is useful in library screening prioritization. Even with lower quality structural information, such as homology model, the technique described herein will still provide useful information.

Figure 8:
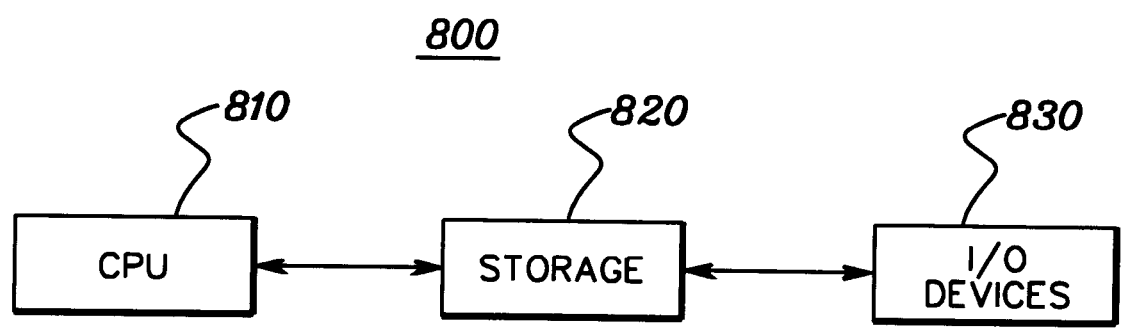
FIG. 8 depicts one embodiment of a computer environment providing and/or using the capabilities of the present invention.

The capability of the present invention can readily be automated by creating a suitable program, in software, hardware, microcode, firmware or any combination thereof. Further, any type of computer or computer environment can be employed to provide, incorporate and/or use the capability of the present invention. One such environment is depicted in FIG. 8 and described in detail below.

In one embodiment, a computer environment 800 includes, for instance, at least one central processing unit 810, a main storage 820, and one or more input/output devices 830, each of which is described below.

As is known, central processing unit 810 is the controlling center of computer environment 800 and provides the sequencing and processing facilities for instruction execution, interruption action, timing functions, initial program loading and other machine related functions. The central processing unit executes at least one operating system, which as known, is used to control the operation of the computing unit by controlling the execution of other programs, controlling communication with peripheral devices and controlling use of the computer resources.

Central processing unit 810 is coupled to main storage 820, which is directly addressable and provides for high-speed processing of data by the central processing unit. Main storage may be either physically integrated with the CPU or constructed in stand-alone units.

Main storage 820 is also coupled to one or more input/output devices 830. These devices include, for instance, keyboards, communications controllers, teleprocessing devices, printers, magnetic storage media (e.g., tape, disk), direct access storage devices, and sensor-based equipment. Data is transferred from main storage 820 to input/output devices 830, and from the input/output devices back to main storage.

The present invention can be included in an article of manufacture (e.g., one or more computer program products) having for instance, computer usable media. The media has embodied therein, for instance, computer readable program code means for providing and facilitating the capabilities of the present invention. The articles of manufacture can be included as part of a computer system or sold separately.

Additionally, at least one program storage device readable by a machine, tangibly embodying at least one program of instructions executable by the machine to perform the capabilities of the present invention can be provided.

The flow diagrams depicted herein are just exemplary. There may be many variations to these diagrams or the steps (or operations) described therein without departing from the spirit of the invention. For instance, the steps may be performed in a differing order, or steps may be added, deleted or modified. All of these variations are considered a part of the claimed invention.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined by the following claims.

The invention claimed is:

1. A computer-aided method of docking a ligand to a protein so as to determine ligand conformations likely to bind to said protein, said method comprising:
    performing a pre-docking conformational search and generating multiple solution conformations of a ligand therefrom;
    generating a binding site image of a protein, said binding site image comprising multiple hot spots;
    matching hot spots of the binding site image to atoms in at least one conformation of the multiple solution conformations of the ligand to initially position said at least one conformation of said ligand as a rigid body into said binding site so as to obtain at least one position of the ligand relative to the protein in a protein-ligand complex;
    optimizing the at least one position of the ligand while allowing translation, orientation and rotatable bonds of the ligand to vary, and while holding the protein fixed;
    calculating a score for the optimized position of the ligand using one or more potential functions;
    selecting one or more optimized ligand positions based on said score;
    wherein said matching comprises:
        matching atoms of the at least one solution conformation of the ligand to appropriate hot spots of the protein by positioning the at least one solution conformation of the ligand as a rigid body into the binding site image;
        defining a match, said match determining a unique rigid bode transformation; and
        using the unique rigid body transformation to place the at least one solution conformation of the ligand into the binding site of the protein; and
    wherein said determining the unique rigid body transformation comprises determining the unique rigid body transformation that minimizes:

$$I(R, T) = \sum_{j=1}^{3} |H_j - RA_j - T|^2$$

where:
    $I(R,T)$=rms deviation between a $j^{th}$ hot spot and a $j^{th}$ atom of the at least one solution conformation of the ligand;
    $H_j$=a position vector of a $j^{th}$ hot spot of the protein;
    $A_j$=a position vector of a $j^{th}$ atom of the at least one solution conformation of the ligand;
    R=a 3×3 rotation matrix; and
    T=a translation vector.

2. At least one program storage device readable by a machine, tangibly embodying at least one program of instructions executable by the machine to perform a method of docking a ligand to a protein so as to determine ligand conformations likely to bind to said protein, said method comprising:

performing a pre-docking conformational search and generating multiple solution conformations of a ligand therefrom;

generating a binding site image of a protein, said binding site image comprising multiple hot spots;

matching hot spots of the binding site image to atoms in at least one conformation of the multiple solution conformations of the ligand to initially position said at least one conformation of said ligand as a rigid body into said binding site so as to obtain at least one position of the ligand relative to the protein in a protein-ligand complex;

optimizing the at least one position of the ligand while allowing translation, orientation and rotatable bonds of the ligand to vary, and while holding the protein fixed;

calculating a score for the optimized position of the ligand using one or more potential functions;

selecting one or more optimized ligand positions based on said score;

wherein said matching comprises:

matching atoms of the at least one solution conformation of the ligand to appropriate hot spots of the protein by positioning the at least one solution conformation of the ligand as a rigid body into the binding site image;

defining a match, said match determining a unique rigid body transformation; and using the unique rigid body transformation to place the at least one solution conformation of the ligand into the binding site of the protein; and wherein said determining the unique rigid body transformation comprises determining the unique rigid body transformation that minimizes:

$$I(R, T) = \sum_{j=1}^{3} |H_j - RA_j - T|^2$$

where:

$I(R,T)$=rms deviation between a $j^{th}$ hot spot and a $j^{th}$ atom of the at least one solution conformation of the ligand;

$H_j$=a position vector of a $j^{th}$ hot spot of the protein;

$A_j$=a position vector of a $j^{th}$ atom of the at least one solution conformation of the ligand;

$R$=a 3×3 rotation matrix; and $T$=a translation vector.

* * * * *

UNITED STATES PATENT AND TRADEMARK OFFICE
CERTIFICATE OF CORRECTION

| | | |
|---|---|---|
| PATENT NO. | : 7,065,453 B1 | Page 1 of 1 |
| APPLICATION NO. | : 09/595096 | |
| DATED | : June 20, 2006 | |
| INVENTOR(S) | : David J. Diller | |

It is certified that error appears in the above-identified patent and that said Letters Patent is hereby corrected as shown below:

Column 18, line 42, in claim 1, which reads "bode", should read -- body --

Signed and Sealed this

Sixth Day of May, 2008

JON W. DUDAS
*Director of the United States Patent and Trademark Office*